United States Patent [19]

Sih

[11] Patent Number: 4,461,835

[45] Date of Patent: Jul. 24, 1984

[54] PROCESS FOR PREPARING OPTICALLY-ACTIVE ISOPRENOID INTERMEDIATES

[75] Inventor: Charles J. Sih, Madison, Wis.

[73] Assignee: Wisconsin Alumni Research Foundation, Madison, Wis.

[21] Appl. No.: 394,970

[22] Filed: Jul. 2, 1982

[51] Int. Cl.$^3$ ............... C07B 19/02; C12R 1/38
[52] U.S. Cl. ............................ 435/280; 435/874
[58] Field of Search ............... 435/280, 874, 262

[56] References Cited

U.S. PATENT DOCUMENTS 3,256,156  6/1966  Frommer et al. ............... 435/280
3,347,752 10/1967  Rauenbush et al. ............ 435/280
4,022,664  5/1977  Kawamura et al. ............. 435/280

OTHER PUBLICATIONS

Oritani et al., "Enzymatic Resolution of (±), Unsaturated Cyclic Tospene Alcohols via Asymmetric Hydrolysis of Corresponding Acetates by Mircoorganisms", *Agric. Biol. Chem.*, vol. 44, No. 11 (1980), pp. 2637–2642.

Cohen et al., "Synthetic Studies on (2R, 4'R, 8'R)-2-Tocophenol, An Approach Utilizing Side Chain Synthons of Microbial Origin", *J. Org. Chem.*, vol. 41, No. 22, (1976), pp. 3505–3511.

*Primary Examiner*—Robert A. Yoncoskie
*Assistant Examiner*—Marianne Minnick
*Attorney, Agent, or Firm*—Howard W. Bremer

[57] ABSTRACT

The invention discloses a method for preparing optically active bifunctional synthons useful in synthesizing natural isoprenodis by resolving racemic substituted aryloxy-α-alkyl esters through the hydrolytic action of microorganisms selected from the orders Endomycetales and Eubacteriales.

15 Claims, No Drawings

PROCESS FOR PREPARING OPTICALLY-ACTIVE ISOPRENOID INTERMEDIATES

DESCRIPTION

TECHNICAL FIELD

This invention relates to isoprenoic intermediates and more particularly to microbiological process for the resolution of racemic substituted aryloxy-α-methyl esters.

More particularly, this invention relates to processes for selectively hydrolyzing one antipode of aryloxy-α-methyl esters to give optically-active aryloxy-α-methyl acids; the remaining esters also being optically active. The chiral intermediates are useful in synthesizing natural isoprenoids such as the isoprenoid side chain of vitamin E.

BACKGROUND ART

In recent years there has been great interest in the design of practical asymmetric syntheses of vitamin E. Consequently much effort has been expended to find more economical routes to produce natural vitamin E. (See for example, H. G. W. Leuenberger, W. Boguth, R. Barner, M. Schmid, R. Zell, *Helv. Chim. Acta*, 62, 455, 1979; N. Cohen, W. F. Eichel, R. J. Lopresti, C. Neukom, G. Saucy, *J. Org. Chem.*, 41, 3505, 1976.) These studies are directed to methods for preparing, from optically-active intermediates of microbial origin, the isoprenoid side chain of vitamin E or α-tocopherol, because it is extremely difficult to introduce the two designated (*) chiral centers via chemical methods. For example, a four carbon chiral synthon (2) derived from (S)-β-hydroxyisobutyric acid and a five carbon chiral synthon (3) prepared via yeast reduction were incorporated into the side chain of α-tocopherol. Both 2 and 3 were prepared using oxidative and reductive processes of microbes.

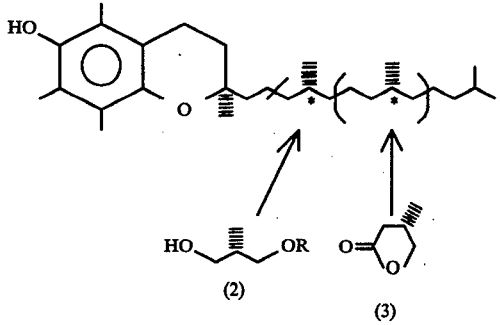

DISCLOSURE OF INVENTION

The process of this invention utilizes the hydrolytic processes of microorganisms and broadly comprises the use of microbial carboxyesterases to selectively cleave the ester grouping of one of the enantiomers of racemic aryloxy-α-methyl ester (4) resulting in a kinetic resolution.

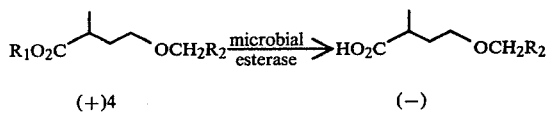

$R_1 = CH_3, C_2H_5, C_3H_7$ and

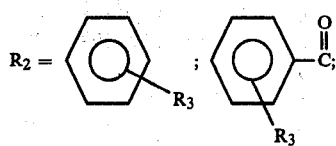

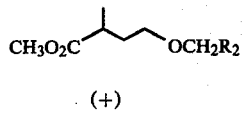

$R_3 = Cl, Br, CH_3, NO_2$

The preferred substrate for the process of this invention comprises α-alkyl carboxylic acid esters substituted with an aryloxy grouping at $C_4$, to provide the hydrophobic group for binding, where, for purposes of the invention alkyl is defined as a hydrocarbon chain having from about 1 to 4 carbon atoms (i.e. in preceding formula (4) $R_1$ can be $CH_3$, $C_2H_5$, $C_3H_7$, $C_4H_9$ and

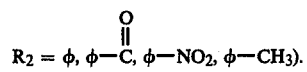

It has also been found that microorganisms which are capable of functioning to cleave the ester molecules as indicated above are those which elaborate hydrolytic enzymes. Examples of such microorganisms which are particularly suitable in the method of this invention are those of the orders Endomycetales and Eubacteriales. Microorganisms such as *Saccharomyces acidifaciens* NRRL Y-7253, *Enterobacter cloacae* NRRL B-15052 and Bacillus sp. NRRL B-15053 have been found to be eminently suitable for the process of this invention.

It is to be understood that the process of this invention is not to be considered as limited to the compounds specifically set forth herein. For example, compounds where the $R_2$ substituent is an hydrophobic unit such as cyclohexane, biphenyl, or naphthyl derivatives, either in the form of ethers or esters, are operable in the process of this invention. Also, combinations of various substituent groups such as $CH_3$, halo, nitro groups on the rings are also operable. In fact, $R_2$ can comprise any hydrophobic unit.

Microorganisms which are characterized by their carboxyesteratic activity are well known in the microbiological art. Reference is particularly made to K. Kieslich, "Microbial Transformations of Non-Steroid Cyclic Compounds" (Georg Thieme Publishers, Stuttgart, 1976). Any of the genera of microorganisms described herein can be employed in the process of this invention. The racemic ester substrate can be incorporated in a nutrient medium of standard composition in which such organisms are cultivated and the usual conditions of fermentation can then be employed to effect the hydrolytic transformation. Alternatively, the active principle can be removed from the growing culture of the microorganism, for instance by lysis of the cells to release the enzymes, or by suspension of the mycelium in a fresh aqueous system. In any of these techniques the $R_1$ ester grouping will be selectively cleaved without cleaving $R_2$, so long as the active principle elaborated by the microorganisms is present in the medium. Of course, the temperature, time and pressure conditions under which the contact of the aryloxy-α-methyl ester derivative with the hydrolytic principle is carried out are interdependent as will be apparent to any one skilled in the art. For instance, with gentle heating and at atmospheric pressure the time required to effect the hydrolytic conversion will be less than if the process is carried out at room temperature, other conditions being the same. Of course, neither temperature, nor pressure, nor time, should be so high that the ester substrate is caused thereby to be degraded. Where a growing culture of the organism is being used, the process conditions should also be sufficiently gentle so the organism is not killed prematurely before it elaborates sufficient hydrolytic enzymes. Generally the temperature can range from about 10° C. to about 35° C., and the time from about 12 hours to about 10 days.

DETAILED DESCRIPTION OF THE INVENTION

The following examples are given by way of illustrating the present invention and are not to be considered as limiting the scope of the appended claims.

Synthesis of racemic methyl 4-benzyloxy-2-methylbutyrate

Scheme

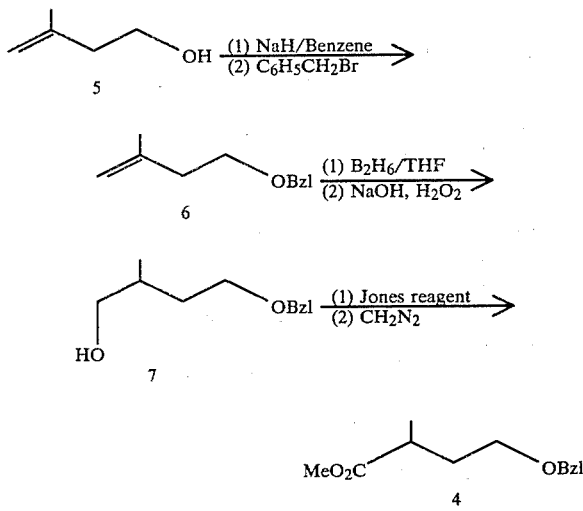

1-O-Benzyl-3-methyl-4-buten-1-ol (6). The prewashed sodium hydride (14.4 g) was suspended in 300 ml of benzene and cooled in ice bath. To this cold sodium hydride suspension, 3-methyl-3-buten-1-ol (5, 25.2 g) (Aldrich) was added slowly with stirring. After the addition, benzyl bromide (56.4 g) was added to the reaction mixture. The resulting reaction mixture was heated at reflux overnight. The excess sodium hydride was destroyed by adding water slowly in ice bath. The benzene layer was separated, and the aqueous layer was extracted thoroughly with ether. The combined organic solution was washed with brine. After removal of the solvent, the crude oil was distilled to yield 45.5 g (80%) of 1-O-benzyl-3-methyl-4-buten-1-ol (6), b.p. 99°–100° C. (10 mm Hg).

1-O-Benzyl-3-methyl-but-1,4-diol (7). A sample of 1-O-benzyl-3-methyl-4-buten-1-ol (6) (45.1 g) was dissolved in 300 ml of THF and cooled in ice bath. To this cold solution, 102 ml of 1M borane-THF solution was added slowly with stirring. The reaction mixture was stirred at room temperature for 1 hour, and cooled in ice bath. The following solutions were added in succession to the cold reaction mixture: 35 ml of $H_2O$, 35 ml of 3N NaOH, and finally 35 ml of 30% $H_2O_2$. The resulting reaction mixture was stirred at 45±5° C. for 2 hours. The organic layer was separated, and the aqueous layer was washed with ether. The combined organic solution was washed with saturated sodium bisulfite solution and brine. After removal of solvent, the crude oil was distilled to give 43 g (85%) of 1-O-benzyl-3-methyl-but-1,4-diol, 7, b.p. 173°–175° C. (10 mm Hg).

Methyl-4-benzyloxy-2-methylbutyrate (4). A sample of 1-O-benzyl-3-methyl-but-1,4-diol (9.7 g) was dissolved in 60 ml of acetone, and cooled in an ice bath. To this cold solution, 41.2 ml of 0.267M Jones reagent was added dropwise with stirring. After stirring at ice bath for 1 hour, excess Jones reagent was destroyed by adding isopropanol. Ether (100 ml) and an adequate amount of water were added with stirring until the solid material was getting into solution. The organic layer was separated, and the aqueous layer was extracted with ether thoroughly. After removal of solvent, the acid was treated with diazomethane without further purification. The resulting crude ester was distilled to yield 9.2 g (83%) of methyl-4-benzyloxy-2-methylbutyrate (4), b.p. 160°–162° C. (10 mm Hg).

This same procedure was repeated for the synthesis of the other substrates described hereinafter by substituting the appropriate aryl bromide for benzyl bromide in the above reation sequence.

EXAMPLE I (BACTERIA)

A. Fermentation. Surface growth from a one week old agar slant of *Enterobacter cloacae* NRRL B-15052 grown on agar of the following composition:

|  | Gms |
| --- | --- |
| Agar | 20 |
| Bacto-beef extract | 3 |
| Bacto-peptone | 5 |
| (Sterilized 15 min at 20 p.s.i.) | | was suspended in 5 ml of an 0.85% saline solution. One ml portions of this suspension were used to inoculate a 250 ml Erlenmeyer flask (F-1 stage) each containing 50 ml of the following medium (Difco nutrient broth):

|  | Gms |
| --- | --- |
| Bacto-beef extract | 3 |
| Bacto-peptone | 5 |
| Distilled water, q.s. 1 liter | |
| pH 6–8 (sterilized for 14 min at 30 p.s.i.) | |

The flasks were incubated at 25° C. on a rotary shaker (250 cycles/min—2" radius) for 24 hours, after which a 10% by volume transfer was made to a 2 liter Erlenmeyer flask containing 500 ml of Difco nutrient broth. Simultaneously, 500 mg of (±)4-benzyloxy-2-methylbutyric acid methyl ester (4) in 0.1 ml of 10% Tween 80 was added resulting in a final substrate concentration of 0.1%. The F-2 stage flasks were then incubated for an additional 96 hours under the conditions used in the incubation of the F-1 stage flasks.

B. Isolation. 96 hours after addition of the substrate, the F-2 stage was terminated by the addition of 6N HCl until the pH of the medium was lowered to 2. The contents were filtered through a pad of celite and the filtrate was extracted with chloroform (3×500 ml). The combined chloroform extracts were dried over sodium sulfate and concentrated in vacuo to give a residue (900 mg). This residue was dissolved in 4 ml of a solvent mixture of Skelly B-ethyl acetate (15:1) and chromatographed over a silica gel (MN Kieselgel 60, Brinkmann) column (1.2×40 cm). The column was eluted with a solvent system comprised of Skelly B-ethyl acetate (15:1) and 18 ml fractions were collected. Fractions 1-5 contained 200 mg of residual (+)-4-benzyloxy-2-methylbutyric acid methyl ester, $[\alpha]_D^{25} +18.2°$ (c, 2.5, CHClH$_3$); ee=0.84; while fractions 16-30 contained 150 mg of (−)4-benzyloxy-2-methylbutyric acid, $[\alpha]_D^{25} -13.4°$ (c, 1.0, CHCl$_3$); ee=0.80.

C. The progress of the microbiological hydrolyses of 4-aryloxy-2-methyl esters can be followed by thin-layer chromatographic analyses using Brinkmann 20×20 cm (EM) plates (0.25 mm thickness) of silica gel containing PF254 indicator. The solvent system used was: ethyl acetate-hexane-acetic acid (50:50:2). R$_f$ of ester≈0.50; R$_f$≈0.29.

D. Determination of Optical Purity. The optical purity expressed as enantiomeric excess (ee) is determined by PMR in the presence of the chiral lanthanide shift reagent, Eu(hfc)$_3$ (Aldrich) as described by C. S. Chen, Y. Fujimoto and C. J. Sih, *J. Am. Chem. Soc.* 1981, 103, 3580.

EXAMPLE 2 (YEASTS)

A. Fermentation. Surface growth from a one week old agar slant of *Saccharomyces acidifaciens* NRRL Y-7523 grown on agar of the following composition:

| | Gms |
|---|---|
| Agar | 20 |
| Glucose | 10 |
| Yeast extract | 2.5 |
| K$_2$HPO$_4$ | 1 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flask (F-1 stage) each containing 50 ml of the following medium (Vogel's medium):

| | Gms |
|---|---|
| Yeast extract | 5 |
| Casamino acids | 5 |
| Dextrose | 40 |
| Na$_3$—citrate-5½ H$_2$O | 3 g |
| KH$_2$PO$_4$ | 5 g |
| NH$_4$NO$_3$ | 2 g |
| CaCl$_2$.2H$_2$O | 0.1 g |
| MgSO$_4$.7H$_2$O | 0.2 g |
| Trace element solution | 0.1 ml |
| Distilled water, q.s. 1 liter | |
| pH 5.6 (sterilized for 15 min at 30 p.s.i.) | |

| Trace element solution | Gm/100 ml |
|---|---|
| Citric acid-1H$_2$O | 5 |
| ZnSO$_4$.7H$_2$O | 7 |
| Fe(NH$_4$)$_2$(SO$_4$)$_2$.6H$_2$O | 1 |
| CuSO$_4$.5H$_2$O | 0.25 |
| MnSO$_4$.1H$_2$O | 0.05 |
| H$_3$BO$_3$ | 0.05 |
| Na$_2$MoO$_4$.2H$_2$O | 0.05 |

The flasks were incubated at 25° C. on a rotary shaker (250 cycles/min—2" radius) for 24 hours, after which a 10% by volume transfer was made to a 2 liter Erlenmeyer flask F-2 stage) containing 500 ml of Vogel's medium. Simultaneously 500 mg of (±)4-benzyloxy-2-methylbutyric acid methyl ester in 0.1 ml of 10% Tween 80 was added, resulting in a final substrate concentration of 0.1%. The F-2 stage flasks were then incubated for an additional 96 hours under the conditions used in the incubation of the F-1 stage flasks.

B. Isolation. 72 hours after the addition of the substrate, the F-2 stage was terminated by the addition of 6N HCl until the pH was lowered to 2.0. The contents were filtered through a pad of celite and the filtrate was extracted with chloroform (3×500 ml). The combined chloroform extracts were dried over sodium sulfate and concentrated in vacuo to yield an oil residue (920 mg). The residue was dissolved in 5 ml of Skelly B-ethyl acetate (15:1) and chromatographed over a silica gel (Kieselgel MN60, Brinkman) column (1.2×35 cm). The column was eluted with Skelly B-ethyl acetate (15:1) and 20 ml fractions were collected. Fractions 1-8 contained 160 mg of (+)4-benzyloxy-2-methylbutyric acid methyl ester, $[\alpha]_D^{25} +17.8°$ (c, 2.0, CHCl$_3$); ee=0.82; fractions 14-32 contained 118 mg of (−)4-benzyloxy-2-methylbutyric acid, $[\alpha]_D^{25} -13.2$ (c, 1.8, CHCl$_3$); ee=0.84.

EXAMPLE 3

Optically active (−)4-benzyloxy-2-methylbutyric acid (ee=0.85) and (+)4-benzyloxy-2-methylbutyric acid methyl ester (ee=0.83) were prepared in accordance with the procedure of Example 1 except that Bacillus sp. NRRL B-15053 was used as the microorganism to effect the stereoselective hydrolysis.

EXAMPLES 4 THROUGH 39

Optically active (−)4-benzyloxy-2-methylbutyric acid and (+)4-benzyloxy-2-methylbutyric acid methyl ester were prepared in accordance with the procedure of Example 1 except that the organisms listed in Tables 1 and 2 were used as the microorganisms to effect the stereoselective hydrolyses.

TABLE 1

Order—Endomycetales

1. *Saccharomyces acidifaciens* NRRL Y-7253
2. *Zygosaccharomyces priorianus* NRRL Y-12,624
3. *Saccharomyces ellipsoides* NRRL Y-12,632
4. *Geotrichum candidum* ATCC 26195
5. *Torula lactosa* NRRL Y-329
6. *Mycoderma cerevisiae* NRRL Y-1615
7. *Endomyces magnusii* NRRL Y-1272
8. *Candida lipolytica* NRRL Y-1095
9. *Candida pseudotropicalis* NRRL Y-1264
10. *Endomyces vernalis* NRRL Y-1485
11. *Hansenula anomala* NRRL Y-366
12. *Saccharomyces lactis* NRRL Y-1140
13. *Rhodotorula sp.* ATCC 20254
14. *Rhodotorula gracilis* ATCC 10788
15. *Hansenula subpelliculosa* NRRL Y-1683
16. *Dipodascus albidus* ATCC 12934
17. *Oidium lactis* NRRL Y-552

18. *Pichia alcoholophilia* NRRL Y-2026

All of these organisms listed are on deposit and may be obtained from Northern Regional Research Laboratory at Peoria, Ill. or from ATCC.

TABLE 2
Order—Eubacteriales

1. Bacillus sp. NRRL B-15053
2. *Bacillus cereus* ATCC 12480
3. *Bacillus brevis* ATCC 8185
4. *Bacillus megaterium* ATCC 19213
5. *Bacillus sphaericus* ATCC 12844
6. *Enterobacter cloacae* NRRL B-15052
7. *Enterobacter aerogenes* ATCC 15038
8. *Flavobacterium* sp. ATCC 13552
9. *Mycobacterium rhodochrous* ATCC 12483
10. *Mycobacterium fortuitum* ATCC 6841
11. *Nocardia restrictus* ATCC 14887
12. *Nocardia corallina* ATCC 13258
13. *Arthrobacter simplex* ATCC 6946
14. Corynebacterium sp. ATCC 21245
15. *Flavobacterium dehydrogenans* ATCC 13930

EXAMPLE 40

The procedure of Example 1 was again employed, this time substituting for the ester reactant an identical quantity of (±)4-nitrobenzyloxy-2-methylbutyric acid methyl ester. Optically active (−)4-nitrobenzyloxy-2-methylbutyric acid and (+)4-nitrobenzyloxy-2-methylbutyric acid methyl ester were obtained.

When the procedure of this Example was repeated with the microorganisms listed in Tables 1 and 2, the same stereoselective hydrolyses were again achieved. Also, with the use of (±)4-chlorobenzyloxy-2-methylbutyric acid methyl ester or 4-bromobenzyloxy-2-methylbutyric acid methyl ester as the reactants, optically active (−)4-chlorobenzyloxy-2-methylbutyric acid and (−)4-bromobenzyloxy-2-methylbutyric acid were respectively obtained.

I claim:

1. A process for preparing optically active bifunctional synthons which comprises revolving aryloxy-α-alkyl esters by exposing said esters in aqueous medium to the hydrolytic action of the carboxyesterases elaborated by a microorganism of the orders Endomycetales and Eubacteriales whereby one antipode of said esters is hydrolyzed to give optically active aryloxy-α-methyl acids and recovering the component optically active isomers.

2. The process of claim 1 wherein the racemic ester is an aryloxy-α-methyl ester.

3. The process of claim 1 wherein the racemic ester is aryloxy-α-ethyl ester.

4. The process of claim 1 wherein the racemic ester is an aryloxy-α-propyl ester.

5. The process of claim 1 wherein the microorganism for effecting the resolution is selected from *Enterobacter cloacae* NRRL B-15052, Bacillus sp. NRRL B-15053 or *Saccharomyces aureofaciens* NRRL Y-7253.

6. The process of claim 1 wherein the microbiological resolution is effected in a growing culture of the microorganism.

7. The process of claim 1 wherein the microbiological resolution is effected in a microorganism-free medium containing the hydrolytic enzyme elaborated by the microorganism.

8. The process of claim 1 wherein the microbiological resolution is effected by immobilized cells of the microorganism.

9. A process for preparing (−)4-aryloxy-2-methylbutyric acid and (+)4-aryloxy-2-methylbutyric acid which comprises cultivating a microorganism selected from the order Endomycetales and Eubacteriales, in an aqueous nutrient medium, under submerged aerobic conditions, in the presence of a compound having the formula

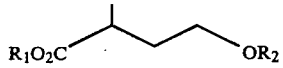

where
$R_1$ is methyl, ethyl or propyl
and $R_2$ is benzyl, nitrobenzyl, chlorobenzyl, bromobenzyl or phenacyl and recovering the component optically active isomers.

10. The process of claim 6 wherein the substrate subjected to microbiological resolution is selected from the group consisting of methyl, ethyl and propyl esters of (±)4-benzyloxy-2-methylbutyric acid and the component optically active isomers are recovered from the fermentation medium.

11. The process of claim 6 wherein the substrate subjected to microbiological resolution is selected from the group consisting of methyl, ethyl and propyl esters of (±)4-*p*-nitrobenzyloxy-2-methyl-butyric acid and the component optically active isomers are recovered from the fermentation medium.

12. The process of claim 6 wherein the substrate subjected to microbiological resolution is selected from the group consisting of methyl, ethyl and propyl esters of (±)4-phenacyloxy-2-methylbutyric acid and the component optically active isomers are recovered from the fermentation medium.

13. The process of claim 6 wherein the substrate subjected to microbiological resolution is selected from the group consisting of methyl, ethyl and propyl esters of (±)4-*p*-bromobenzyloxy-2-methylbutyric acid and the component optically active isomers are recovered from the fermentation medium.

14. The process of claim 6 wherein the substrate subjected to microbiological resolution is selected from the group consisting of methyl, ethyl and propyl esters of (±)4-o-chlorobenzyloxy-2-methylbutyric acid and the component optically active isomers are recovered from the fermentation medium.

15. The process of claim 6 wherein the substrate subjected to microbiological resolution is selected from the group consisting of methyl, ethyl and propyl esters of (±)4-*p*-chlorobenzyloxy-2-methylbutyric acid and the component optically active isomers are recovered from the fermentation medium.

* * * * *

UNITED STATES PATENT OFFICE
CERTIFICATE OF CORRECTION

Patent No. 4,461,835        Dated July 24, 1984

Inventor(s) Charles J. Sih

It is certified that error appears in the above-identified patent and that said Letters Patent are hereby corrected as shown below:

Insert the following paragraph as the first paragraph of the specification in Column 1:

--This invention was made with Government support under NIH Grant Nos. AM09688, GM26838 and HL25772. The Government has certain rights in this invention.--

Signed and Sealed this

Twenty-seventh Day of November 1984

[SEAL]

Attest:

Attesting Officer

GERALD J. MOSSINGHOFF

Commissioner of Patents and Trademarks